United States Patent [19]
Reinstein et al.

[11] Patent Number: 5,293,871
[45] Date of Patent: Mar. 15, 1994

[54] SYSTEM FOR ULTRASONICALLY DETERMINING CORNEAL LAYER THICKNESSES AND SHAPE

[75] Inventors: Dan Z. Reinstein, New York; Ronald H. Silverman, Brooklyn, both of N.Y.; Donald J. Coleman, Haworth; Frederic L. Lizzi, Tenafly, both of N.J.

[73] Assignees: Cornell Research Foundation Inc., Ithica; Riverside Research Institute, New York, both of N.Y.

[21] Appl. No.: 89,781

[22] Filed: Jul. 9, 1993

Related U.S. Application Data

[63] Continuation-in-part of Ser. No. 59,083, May 5, 1993.

[51] Int. Cl.$^5$ ................................................ A61B 8/10
[52] U.S. Cl. ............................................... 128/660.06
[58] Field of Search ..................... 128/660.03, 660.06, 128/660.09, 660.07; 364/413.25; 73/602, 609, 861.25

[56] References Cited

U.S. PATENT DOCUMENTS 4,676,105  6/1987  Matzuk .................................. 73/602
4,866,614  9/1989  Tam ................................... 364/413.25

OTHER PUBLICATIONS

"Comparison of a Computer-Assisted Laser Pachometer With Two Ultrasonic Pachometers in Normal Corneas", Gritz et al., Refractive & Corneal Surgery, vol. 6, Jan./Feb. 1990, pp. 9–14.
"Advances in the Analysis Of Corneal Topography", Wilson et al., Survey of Opthamology, vol. 35, No. 4, Jan./Feb. 1991, pp. 269–277.
"Corneal Thickness Profiles in Rabbits Using and Ultrasonic Pachometer", Chan et al., Investigative Ophthalmology and Visual Science, vol. 24, Oct. 1983, pp. 1408–1410.
"Theoretical Framework For Spectrum Analysis In Ultrasonic Tissue Characterization", Lizzi, et al., J. Acoust. Soc. Am. 73 (4), Apr. 1983, pp. 1366–1373.
"Improved Ultrasonic Detection Using The Analytic Signal Magnitude", Gammell, Ultrasonics, Mar. 1981, pp. 73–76.
"Tissue Characterization With Ultrasound", Greenleaf, editor, CRC Press, 1986, pp. 42–60.
"Determination Of The Corneal Thickness Profile By Optical Pachometry", Edmund, Acta Ophthalmologica, vol. 65, (1987), pp. 147–152.
"Methods of Analysis of Corneal Topography", Klyce et al., Refractive & Corneal Surgery, vol. 5, Nov./Dec. 1989, pp. 368–371.

Primary Examiner—William E. Kamm
Assistant Examiner—George Manuel
Attorney, Agent, or Firm—Perman & Green

[57] ABSTRACT

An ultrasound system that enables determination of layer thicknesses and contours of a multi-layer organic body includes a transmitter/receiver for obtaining a radio frequency signal from echoes over a plurality of points on the organic surface. Each radio frequency signal is then deconvolved to remove apparatus generated noise and filtered to create an analytic signal that exhibits a magnitude related to an instantaneous rate of arrival of total echo energy received by the transmitter/receiver. Analytic signals from adjacent parallel scans are then cross-correlated and magnitude detected to determine energy peaks to enable accurate determination of echo producing surfaces of each layer of the multi-layer organic body across the plurality of interrogation points. In the application of the invention to Corneal Epithelium Mapping, a pupil monitoring system is included that disables the measurement system if the pupil's gaze wanders so as to cause a diversion of the optical axis.

9 Claims, 6 Drawing Sheets

SYSTEM FOR ULTRASONICALLY DETERMINING CORNEAL LAYER THICKNESSES AND SHAPE

This application is a continuation-in-part of U.S. patent application, Ser. No. 08,059,083 filed May 5, 1993.

FIELD OF THE INVENTION

This invention relates to ultrasonography, and more particularly, to an ultrasonic device for accurately determining individual layer thicknesses and shape of a patient's cornea.

BACKGROUND OF THE INVENTION

The human corneal epithelium consists centrally of five layers of squamous cells with a thickness in the range of 50 to 60 microns. Peripherally, the human corneal epithelium consists of eleven or more layers. With the onset of surgical treatments to the surface of the cornea, e.g., radial keratotomy, excimer laser shaping of the external surface of the cornea, etc., it has become vitally important to have an accurate map of thickness and contour variations of the various corneal layers.

Slit-lamp micropachymetry is presently the most widely used method for measuring the thickness of the corneal epithelium and corneal scarring. Such micropachymetry and other optical pachymetric methods suffer from a widely varying measurement reproducability, even in the hands of experienced users. For instance, precision for slit-lamp corneal pachymetry has been reported to vary between 5.6 and 19 microns for the same surface. Furthermore, optical methods exhibit the disadvantages of being limited to situations where the media is optically transparent—a condition not often present in areas of corneal scarring.

High frequency ultrasound scanning for imaging and pachymetry of the corneal epithelium was first Ultrasound Microscopic Imaging of the Intact Eye" *Ophthalmology*, Vol. 97, pages 224–250 (1990). In the Pavlin et al. system, measurements were made from B-scans and exhibited a loss of precision due to analog pre-processing of ultrasound signals, i.e., rectification and smoothing.

Lizzi et al. in "Theoretical Framework for Spectrum Analysis in Ultrasonic Tissue Characterization" Journal, *Acoustical Society of America*, Vol. 73 No. 4, pages 1,366–1,373 (1982) describe a clinical ultrasound system which employs deconvolution of a received signal to improve signal quality. Deconvolution, or inverse filtering, was used to compensate for system bandwidth limitations and acted to suppress out-of-band noise and to remove signal anomalies from a received echo. While deconvolution improved resolution of a received signal by removal of extraneous system-derived signals, it did not improve the distinctiveness of echo peaks. Such peaks are critical to accurately determining interfaces between various epithelial layers.

In 1981, Gammell introduced the use of an "Analytic Signal" into the processing of ultrasonic signals. (See "Improved Ultrasonic Detection Using the Analytic Signal Magnitude", *Ultrasonics*, March 1981, pages 73–76). Gammell indicated that previously employed full-wave rectification of a received pulse echo, followed by signal smoothing employing a filter, hindered the resolution of closely spaced tissue interfaces. Gammell indicated that when an electronic signal was treated as an analytic signal, the real signal was replaced by a complex form of both real and imaginary parts. Gammell stated that it was known that the analytic signal correlated to the rate of arrival of energy, i.e., that the square of the magnitude of the analytic signal was proportional to the instantaneous rate-of-arrival of the total energy of the reflected signal. He contrasted this result to the fact that the square of the real signal, was proportional to the rate of arrival of only one of the components of the energy. As a result, the square of the real signal was zero in any instant when one of the component energies was zero, whereas the square of the analytic signal magnitude was only zero when the total instantaneous energy was zero. As a result, use of the analytic signal magnitude enabled optimal estimation of interface location due to the more accurate representation of instantaneous returned energy. However, Gammell employed the analytic signal in lieu of rectification of the ultrasound signal.

To determine analytic signal magnitudes, Gammell took advantage of certain symmetry properties of the Fourier transform of analytic signals. The Fourier transform of a complex ultrasonic signal can be obtained from the Fourier transform of one of its components, by suppressing the negative frequency contributions. The Fourier transform of a real signal is always a symmetrical function, with a total frequency bandwidth of twice the central Fourier frequency. Therefore, the obtaining of the full complex analytic signal was performed by first Fourier transforming the real echo data using a complex fast Fourier transform procedure. Then, all negative frequency components of the Fourier spectrum were set equal to zero and an inverse fast Fourier transform was performed to reconstruct the full analytic signal. The magnitude of the analytic signal was then calculated as the square root of the sum of the squares of the real and imaginary parts at each point in time.

Lizzi et al. further combined signal deconvolution and analytic signal processing to further enhance echo signal data—See "Ultrasonic Ocular Tissue Characterization" pages 41–61, especially pages 45, 46 in "Tissue Characterization with Ultrasound" Greenleaf, editor, CRC Press, 1986.

Thus, to summarize the known prior art, Gammell disclosed that the analytic signal was useful for increasing the resolution of tissue interfaces. Gammell indicated that the analytic signal and its analysis should be used as an alternative to rectification and not in addition thereto. Lizzi et al. taught that ultrasonic tissue characterization could be improved by deconvolving a received scan to remove system-created anomalies and further processed the scan by deriving an analytic signal therefrom.

Notwithstanding the above described prior art echo enhancement procedures, advances in refractive surgery, and in particular excimer laser corneal ablation, provide the surgeon with an ability to remove corneal tissue layers with sub-micron accuracy. Considering that the corneal epithelium has an approximate thickness of 50 microns, it is easily understood that local epithelial thicknesses must be accurately assessed to assure that the laser ablation mechanism is properly controlled. This requires higher levels of resolution of corneal layers than has been heretofore achieved.

Accordingly, it is an object of this invention to provide an improved ultrasound imaging system, particularly adapted to imaging of corneal structures.

It is a further object of this invention to provide an improved ultrasound instrument, having a substantially improved resolution capability.

SUMMARY OF THE INVENTION

An ultrasound system that enables determination of layer contours and thicknesses of a multi-layer organic body includes a transmitter/receiver for obtaining a radio frequency signal from echoes over a plurality of points on the organic surface. Each radio frequency signal is then deconvolved to remove apparatus generated noise and filtered to create an analytic signal that exhibits a magnitude related to an instantaneous rate of arrival of total echo energy received by the transmitter/receiver. Analytic signals from adjacent parallel scans are then cross-correlated and magnitude detected to determine energy peaks to enable accurate determination of echo producing surfaces of each layer of the multi-layer organic body across the plurality of interrogation points. In the application of the invention to Corneal Epithelium Mapping, a pupil monitoring system is included that disables the measurement system if the pupil's gaze wanders so as to cause a diversion of the optical axis.

DETAILED DESCRIPTION OF THE INVENTION

Figure 1:
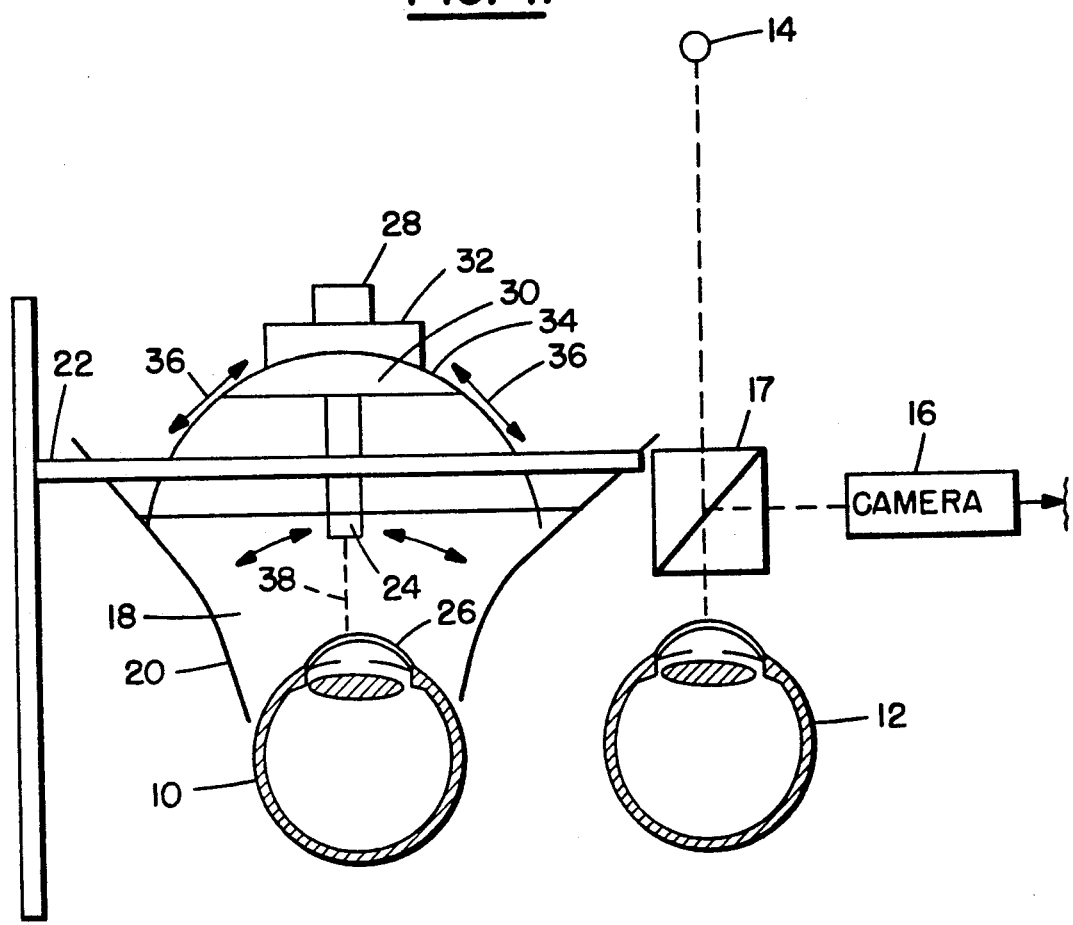
FIG. 1 is a schematic view of apparatus that incorporates the invention.

Referring to FIG. 1, a schematic drawing of a system is schematically shown that incorporates the invention and is positioned over a supinely positioned patient. An eye 10 whose cornea is to be mapped is provided with a drop of topical anesthetic and is held open with a lid speculum. The patient is instructed to focus his other eye 12 upon a fixation light 14 so as to provide a vertical direction of gaze for both eyes 10 and 12. A beam splitter 16 is positioned between eye 12 and light source 14 and enables the pupil of eye 12 to be imaged by a camera 16. By monitoring the pupillary position of eye 12, the pupillary position of eye 10 can be implied and the system automatically disabled should the patient's gaze wander from a vertical axis.

A normal saline water bath 18 is established around eye 10 by the use of a sterile drape 20 that is supported by a ring stand 22. The scanning system is illustrated schematically and comprises a high frequency ultrasonic transducer 24 which is spherically focused onto the surface of cornea 26. Transducer 24 is attached to a motion control system that comprises a linear translation motor 28 and an arc translation motor 30 that are aligned at right angles to each other. Translation motor 30 causes a carriage 32 (to which transducer 24 is affixed) to move bilaterally along a curved track 34 in the directions shown by arrows 36. Translational motor 28 is also affixed to carriage 32 and enables the movement of transducer 24 both into and out of the plane of the paper.

Track 34 is designed to closely follow, if not duplicate, the curvature of cornea 26. Thus, as transducer 24 is moved along track 34 by carriage 32, ultrasonic beam 38 will remain substantially perpendicular to the surface of cornea 26. The perpendicularity of beam 38 assures that oblique reflections from corneal surface 26 are minimized so as to maximize the reflected signal energy. In addition, perpendicularity further enables precise corneal thickness measurements to be obtained.

Figure 2:
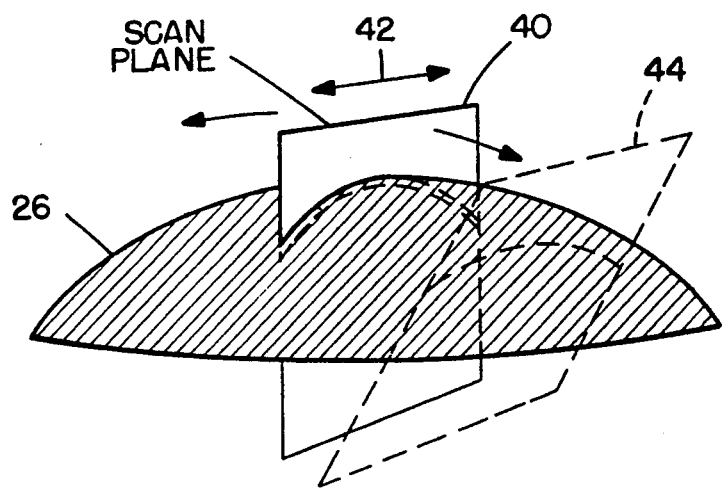
FIG. 2 is a perspective view of a cornea, indicating a direction of scans of an ultrasonic transducer.

In FIG. 2, a perspective view is shown of cornea 26 with a scan plane 40 illustrating the direction of motion of transducer 24. Transducer 24 makes a complete scan of cornea 26 along the axis indicated by arrows 42 for each radial position of scan plane 40. Thus, after a full scan along axis 42 has been completed, transducer 24 is moved to create a new scan plane 44 (shown dotted) by translational motor and translational motor 28 then causes an additional full scan to be accomplished.

Figure 3:
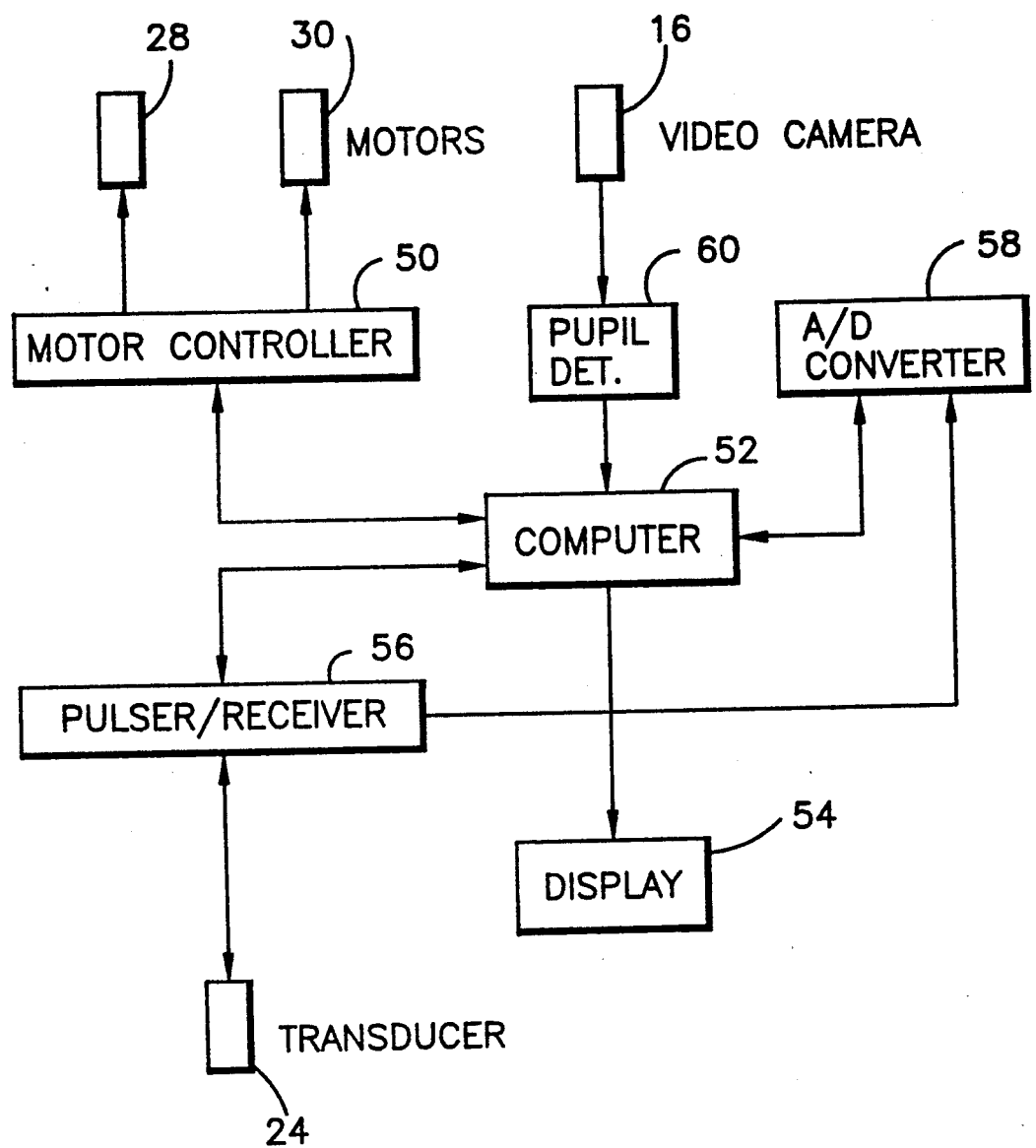
FIG. 3 illustrates a block diagram of electrical portions of the system of FIG. 1.

Referring to FIG. 3, translational motors 28 and 30 are connected to a motor controller 50 whose operation is, in turn, controlled by a computer 52. A display 54 provides an ability to visualize various individual A-type or B-type scans of cornea 26. A pulser/receiver 56 controls transducer 24 in the known manner and provides an output to A/D converter 58 wherein analog scan signals are converted to a plurality of sampled digital values. Computer 52 is provided with digitized scan values after they are accumulated by A/D converter 58 and then is operated to determine the contours and thicknesses of various layers of cornea 26 over the scanned portions of its surface.

Due to the micron level dimensions being analyzed, transducer 24 provides a very high frequency output (e.g., 50 MHz or more). Transducer 24 is initially positioned so as to be vertically oriented over cornea 26. The ultrasonic echoes are amplified by pulser/receiver 56 and may be displayed to initially enable adjustment of the range of transducer 24 from the eye so that the focal point of beam 38 is on or just anterior to the surface of cornea 26.

Amplification gain of pulser/receiver 56 is adjusted so that the observed echoes are of maximum amplitude, but are not clipped, i.e., not beyond voltage range of A/D converter 58. After transducer 24 is aligned, computer 52 is actuated to commence an automatic scan mode wherein pulser/receiver 56 is placed in an externally triggered mode. Computer 52 then begins to issue commands to motor controller 50 such that motors 28 and 30 cause transducer 24 to perform a series of parallel, arc shaped scans across cornea 26 at fixed spatial intervals.

During each arc scan, pulser/receiver 56 emits single interrogating ultrasonic pulses at regularly spaced spatial intervals. For each interrogating ultrasonic pulse, an echo is received which is passed to A/D converter 58 which sequentially samples the echo and provides digitized echo data to computer 52. As an example, A/D converter 58 may sample the received echo signal at the rate of 200 MHz so as to provide 2048 eight bit samples per echo of digitized data to computer 52. A/D converter 58 contains (not shown) a high speed 256k byte, high speed memory which stores digitized echo values from a single scan. After each arc-scan, the 256k bytes are transferred to computer 52 and are stored in random access memory (RAM) stored therein.

Prior to scanning, the patient is instructed to gaze at a fixation light 14 placed vertically above beam splitter 17. The pupillary position of eye 12 is monitored by camera 16 and is fed to a pupil detector 60 shown in FIG. 3. Pupil detector 60 includes a microprocessor and an image buffer which enable successive pupil scans to be compared and for deviations therein to be detected and signaled to computer 52. During scanning, the pupil position of eye 12 is monitored at regular intervals during each arc scan and compared against a previously determined vertical gaze position that is acquired initially. If the pupillary position is found to have deviated by more than a set tolerance level (e.g., 0.25 mm), scan motion and data acquisition are interrupted and pupillary direction is monitored until the gaze is again within tolerance, at which time scanning is continued. Since in most cases, the optical axes of eyes 10 and 12 are parallel, any wandering in the gaze of eye 12 indicates a similar wandering in the gaze direction of eye 10. Thus, this procedure ensures that no significant drift in eye direction occurs during scanning.

Figure 4:
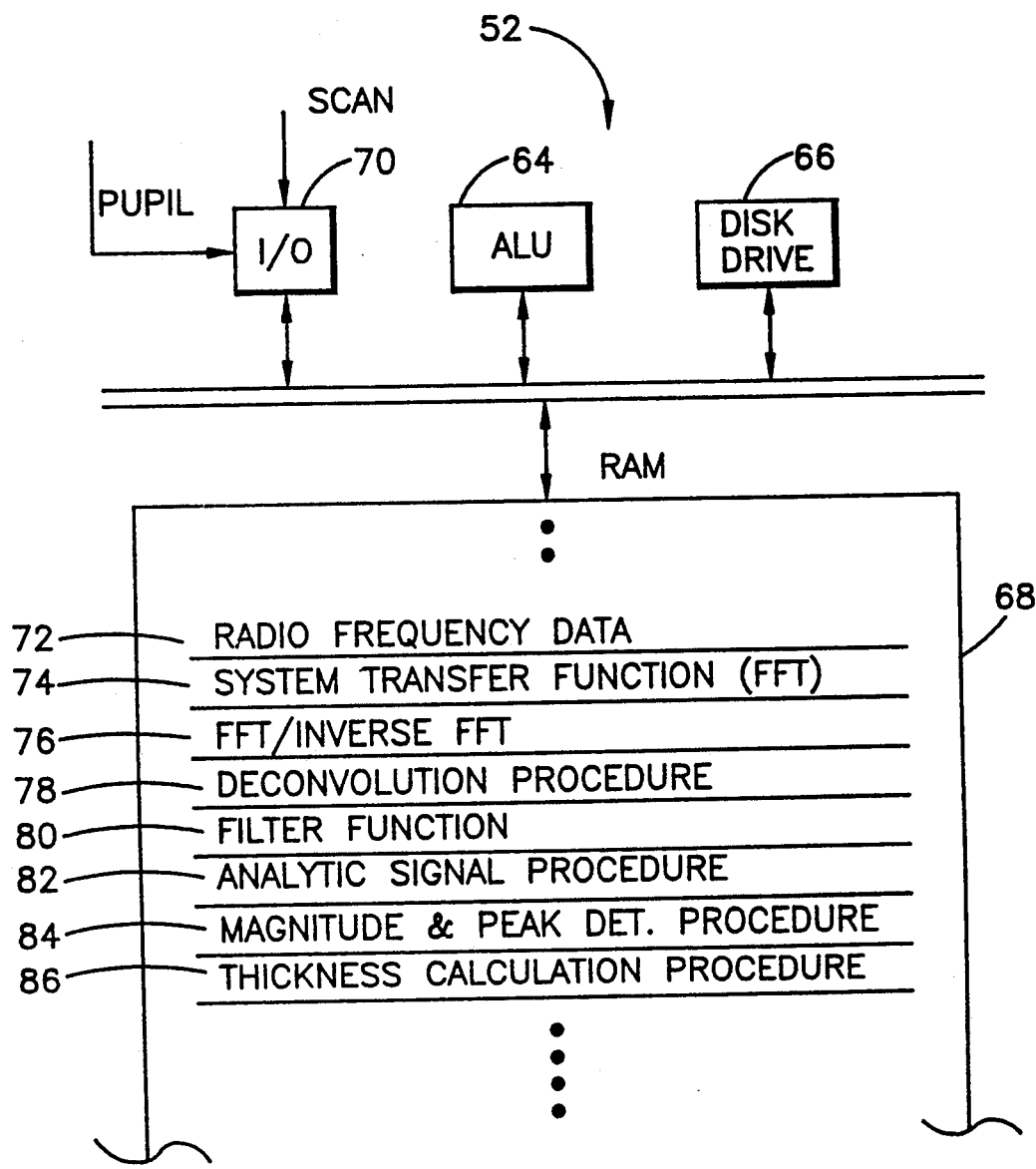
FIG. 4 is a block diagram showing further details of the computer shown in FIG. 3.

Referring now to FIG. 4, certain details of computer 52 will be described that are relevant to analysis of echo scan data. Computer 52 includes an arithmetic logic unit 64, disk drive 66, and random access memory (RAM) 68. Both scan data from A/D converter 58 and pupil data from pupil detect module 60 (FIG. 3) are fed to computer 52 via input/output module 70.

Analysis of parallel scan data involves a number of procedures that enable the scan data to provide highly accurate indications of tissue interface echoes. Those procedures are carried out by subroutines that are found in RAM 68 and operate upon radio frequency data 72 stored therein. Initially, Fourier transform 74 of the transfer function of the ultrasound system shown in FIGS. 1 and 3 is stored for subsequent performance of a deconvolution procedure, wherein system-generated artifacts are removed from the received radio frequency data.

A fast Fourier transform (FFT)/inverse FFT procedure 76 is stored for converting the radio frequency data to the frequency domain. The radio frequency data, after conversion, is subjected to a deconvolution procedure wherein the system transfer function's FFT values are removed from the FFT of the radio frequency data to eliminate system-generated noise therefrom. A prestored filter function 80 is stored in RAM 68 and defines a bandpass that eliminates all negative frequency values that results from the FFT conversion of the radio frequency data. The application of filter function 80 to the FFT of the deconvolved radio frequency data is performed by analytic signal procedure 82 which enables the derivation of an analytic signal from the radio frequency data. The latter procedure includes an inverse FFT operation that provides a temporal analytic signal.

The temporal analytic signal is then subjected to both magnitude and peak determination procedures (employing a cross-correlation operation) to identify reflection peaks. Finally, these peak positions are used to define the surfaces of individual corneal layers. From these surface positions, the shape and thickness of individual corneal layers is derived.

Prior to commencing the analysis of a series of corneal radio frequency, a system transfer function is derived to enable a subsequent removal from the radio frequency signal of system-derived artifacts. The system transfer function is achieved by pointing transducer 24 at a flat glass plate which has been immersed in a water bath. Transducer 24 has its point of focus fixed on the surface of the glass plate and the resulting echo is digitized and stored. The system transfer function is then achieved by subjecting the resulting echo to an FFT analysis to convert the signal to the frequency domain. That FFT transfer function is then stored for subsequent use in a deconvolution procedure.

Figure 5:
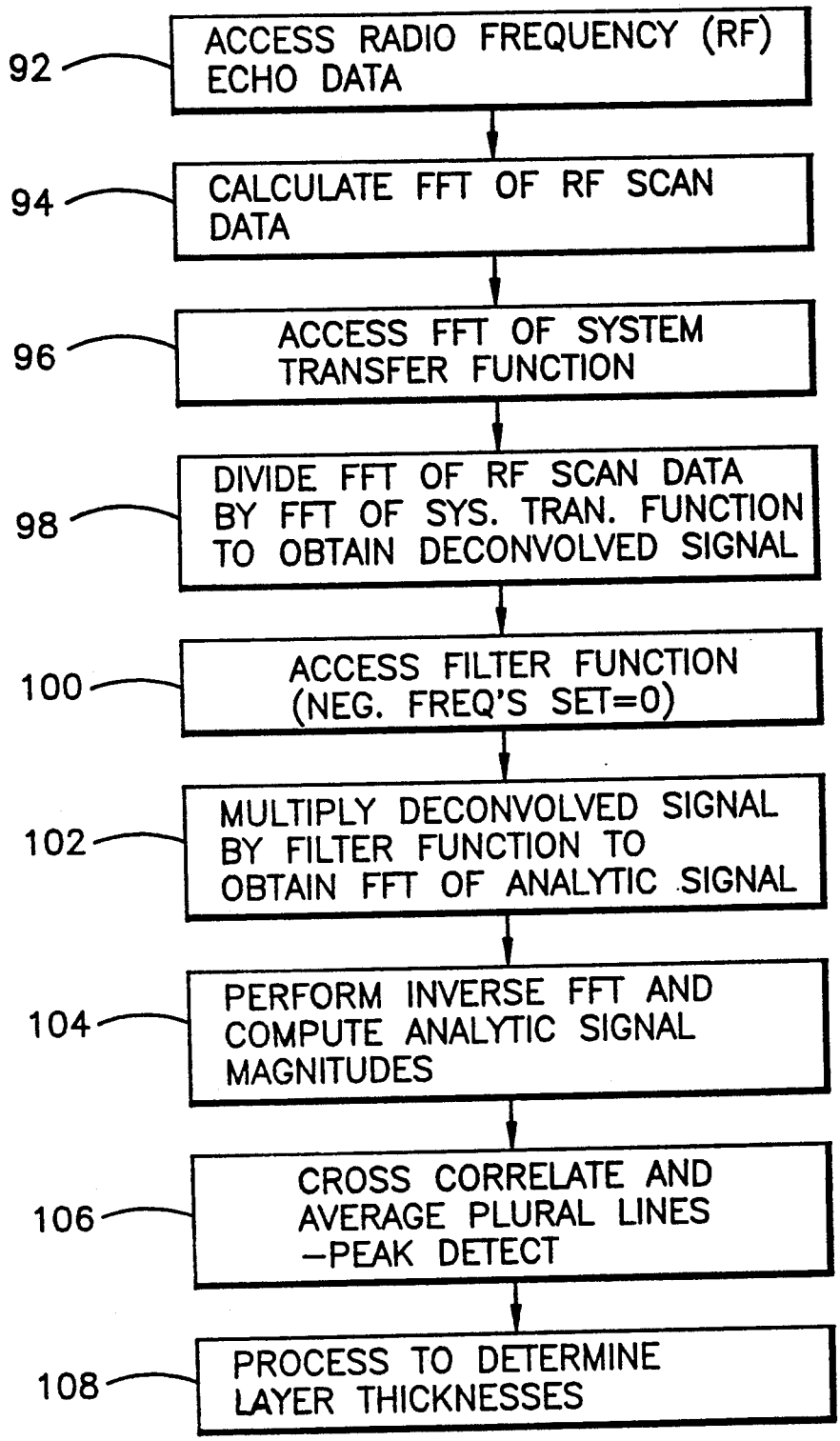
FIG. 5 is a high level logical flow diagram helpful in understanding the operation of the invention.
Figure 7A:
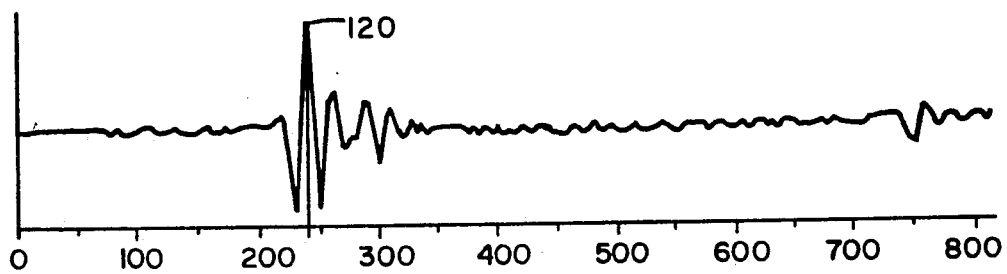
FIGS. 7A-7C illustrate waveforms, helpful in understanding the operation of the invention.

Referring now to the flow diagram of FIG. 5, a digitized radio frequency echo is accessed and inserted into RAM 68 (box 92). As shown in FIG. 7a, the radio frequency data includes both positive and negative going components (shown in analog form). Note that the peak of waveform 120 is at approximately 240 microns and that no subsequent peak clearly illustrates the boundary between the cornea's epithelium and stroma. As will be hereinafter shown, further processing will indicate that the actual corneal surface resides at 250 microns (not 240 microns) and that the boundary between the epithelium and stroma lies at 300 microns.

Next an FFT of the radio frequency data is calculated to convert the temporal signal waveform shown in FIG. 7a to a frequency domain waveform (box 94). Assuming a 50 MHz center frequency for transducer 24, those skilled in the art will understand that the actual output from transducer 24 is a band of frequencies that spans approximately $+/-25$ MHz about the 50 MHz center frequency. The FFT procedure produces a frequency domain waveform where negative frequency components of the scan signal are complex conjugates of the corresponding positive frequency components. The negative frequency components will be subsequently eliminated by application of a filter function; however, prior to that operation, the frequency domain FFT transform is deconvolved by removing system-generated signal components therefrom. This procedure is accomplished by accessing the FFT of the system transfer function (box 96) and dividing the FFT of the radio frequency data thereby. The division of one Fourier transform by another is equivalent in the time domain to a deconvolution that effectively removes system-generated artifacts from the radio frequency echo data (box 98).

Figure 6:
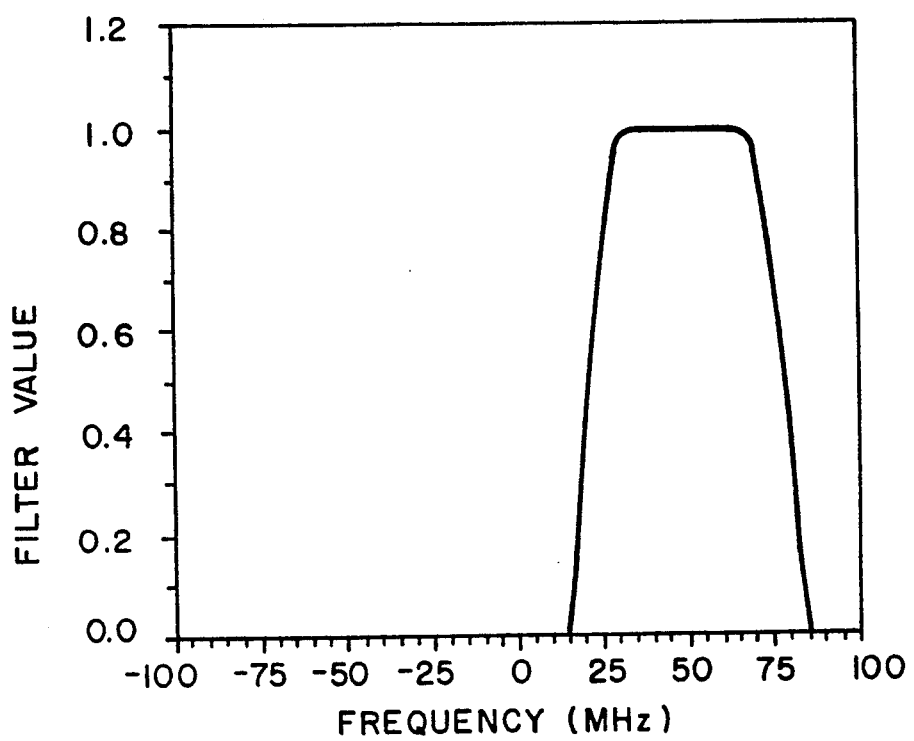
FIG. 6 illustrates the frequency band pass of a filter function employed to derive an analytic signal from a returned echo trace.

At this point, a filter function with negative frequency components set equal to zero is accessed (box 100). The frequency response characteristic of the filter function takes the form shown in FIG. 6. The deconvolved FFT of the radio frequency data is then multiplied by the filter function to obtain an FFT of the analytic signal (box 102). The filter function is set equal to zero in frequency ranges where low signal-to-noise ratios are present.

Figure 7B:
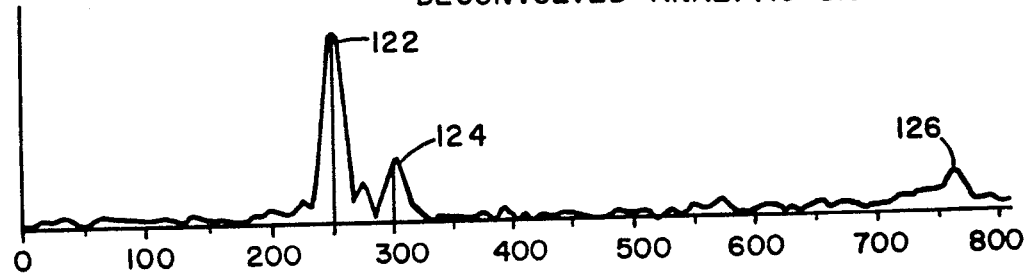
Figure 7C:
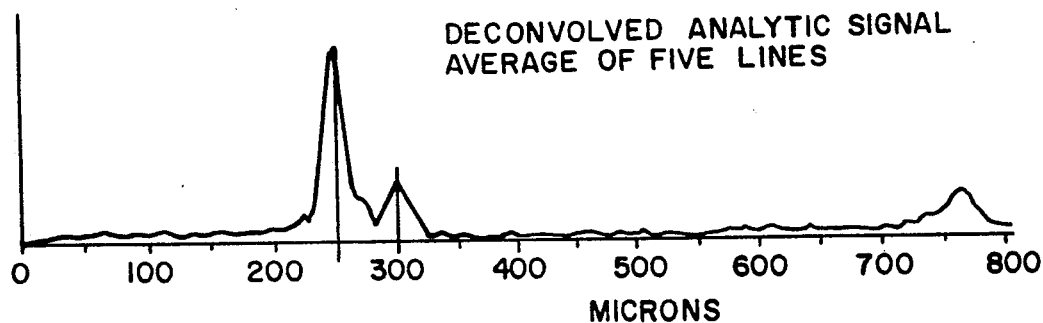

The Fourier transform of the analytic signal is then subjected to an inverse FFT to create a temporal analytic signal (box 104) as 'shown in FIG. 7b. Note that peaks 122 and 124 clearly illustrate the anterior and posterior boundaries of the epithelium and that peak 126 illustrates the posterior boundary of the stroma. To further improve the waveshape, plural adjacent scan lines (e.g. 5) are temporally aligned, added and then averaged (box 106) to enhance the resulting signal to noise ratio (see FIG. 7c). Because distances between a corneal surface and an ultrasonic transducer vary from scan line to scan line, there is often an offset, over adjacent scans, in the observed peaks. This offset must be corrected to assure highly accurate measurements. To accomplish this signal improvement, temporal alignment of adjacent scan lines (e.g. 3 lines, 5 lines etc.) is performed by cross-correlating a series of adjacent analytic signal scan lines, followed by a time shift of the signals to obtain optimal radio frequency analytic signal trace alignments. Subsequently, the adjacent aligned signals are added and averaged.

The digital magnitudes of the averaged signal waveform are now analyzed to detect the peaks of the resulting return signals, with the peaks being used to calculate tissue thicknesses and contours (box 108).

The processed scan results can then be displayed. Clinically useful results consist of the absolute positions about each corneal surface, the rates of curvature of these surfaces, and the thickness of each layer: the epithelium distance between the corneal surface and Bowman's membrane, the stroma (distance between Bowman's membrane and the posterior surface), and the corneal overall (distance between the anterior and posterior corneal surfaces). Several display modalities may be used: the corneal map may be displayed in false-color where a range of colors is used to represent the range of a specified corneal parameter. Such parameter might be a contour map of the cornea. Numeric information, such as the thickness of the cornea at a specified site may also be obtained interactively by cursor movement. Superimposition of the pupil position on a map also provides a useful landmark as the position of the iris (hence the pupil) is apparent in ultrasound images and may be utilized. Demarkation of the pupil's boundary in the scan set produces a set of positional values to which a circle can be fit using the method of least squares. This circle can be included in the topographic in pachymetric maps.

The above described process not only enables the analysis of corneal dimensions and topology, it also can be used to depict corneal pathology such as the position and depth of corneal scars. Experimental verification has indicated that the above procedure enables precision pachymetry of corneal interfaces with a precision of +/−2 microns. It further enables spatial pachymetry of individual corneal layers, both normal and pathological and provides a simultaneous keratometry of anterior/posterior and internal corneal interfaces.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. Ultrasonic apparatus for enabling determination of layer contours and thicknesses of a multilayer organic body, said ultrasonic apparatus comprising:
   transmitter/receiver means for obtaining a plurality of radio frequency signal traces, each radio frequency signal trace derived from echoes over a plurality of points on said organic body;
   means for removing from each radio frequency signal trace, ultrasonic apparatus-generated artifacts to create a deconvolved signal trace;
   filter means for modifying each said deconvolved signal trace to create an analytic signal trace that exhibits a magnitude related to an instantaneous rate of arrival of total echo energy received by said transmitter/receiver means; and
   magnitude detection means for cross-correlating adjacent radio frequency analytic signal traces and shifting said radio frequency analytic signal traces to bring them into temporal alignment,
whereby energy peaks of said analytic signal traces are enhanced so as to enable accurate determination of echo producing surfaces of each layer of said multi-layer organic body, across said plurality points.

2. An ultrasonic apparatus as recited in claim 1 wherein said magnitude detection means averages plural, adjacent temporally aligned radio frequency analytic signal traces to derive an optimum radio frequency analytic signal trace for analysis.

3. An ultrasonic apparatus as recited in claim 2 wherein said means for removing comprises:
   means for deriving a Fourier transform of a transfer function of said ultrasonic apparatus; and
   means for deriving a Fourier transform of a said radio frequency signal trace and for dividing said Fourier transform of said radio frequency signal trace by said Fourier transform of said system transfer function to enable removal therefrom of ultrasonic apparatus-generated artifacts.

4. The ultrasonic apparatus as recited in claim 3 wherein said filter means includes a filter function that evidences a bandpass encompassing only positive components of a Fourier transform of said deconvolved signal, said filter function being applied to said deconvolved signal trace to eliminate negative frequency components therefrom so as to create said analytic signal trace.

5. The ultrasonic apparatus as recited in claim 4 wherein said filter means further converts said filtered, deconvolved signal to a temporal signal.

6. The ultrasonic apparatus as recited in claim 5 wherein said multilayer organic body is a cornea and said magnitude detection means enables peak detections to occur of reflections from corneal anterior and posterior surfaces, an interface between a corneal epithelium and stroma layers and pathologic layers, such as corneal scars.

7. The ultrasonic apparatus as recited in claim 1 wherein said ultrasonic apparatus is utilized for imaging an eye's cornea, said ultrasonic apparatus further comprising:
   means for determining pupillary position of said eye; and
   means for inhibiting operation of said transmitter receiver means when it is determined that said pupil moves by more than a predetermined threshold from a desired orientation.

8. The ultrasonic apparatus as recited in claim 7 wherein said means for determining comprises:
   a source of light positioned over a patient's companion eye to the eye that is being imaged; and
   camera means for viewing the pupil of said companion eye and for providing a signal when said pupil wanders from a predetermined position by a threshold amount.

9. The ultrasonic apparatus as recited in claim 8 wherein said means for inhibiting responds to said signal by interrupting a scanning action of said transmitter receiver means.

* * * * *

UNITED STATES PATENT AND TRADEMARK OFFICE
CERTIFICATE OF CORRECTION

PATENT NO. : 5,293,871
DATED : March 15, 1994
INVENTOR(S) : Dan Z. Reinstein, et al.

It is certified that error appears in the above-indentified patent and that said Letters Patent is hereby corrected as shown below:

Column 1, line 5:
After the Title of the Invention please insert the following:

--This invention was made with Government support under Grant No. EY-01212, awarded by the National Institutes of Health.--

Signed and Sealed this

Thirteenth Day of December, 1994

Attest:

BRUCE LEHMAN

Attesting Officer

Commissioner of Patents and Trademarks